US009335292B2

(12) United States Patent
Hu et al.

(10) Patent No.: US 9,335,292 B2
(45) Date of Patent: May 10, 2016

(54) ELECTROCHEMICAL PROXIMITY ASSAY

(71) Applicant: Auburn University, Auburn, AL (US)

(72) Inventors: Jiaming Hu, Auburn, AL (US); Tanyu Wang, Lawrence, KS (US); Christopher J. Easley, Auburn, AL (US); Curtis G. Shannon, Auburn, AL (US)

(73) Assignee: AUBURN UNIVERSITY, Auburn, AL (US)

( * ) Notice: Subject to any disclaimer, the term of this patent is extended or adjusted under 35 U.S.C. 154(b) by 685 days.

(21) Appl. No.: 13/650,303

(22) Filed: Oct. 12, 2012

(65) Prior Publication Data

US 2014/0102915 A1    Apr. 17, 2014

Related U.S. Application Data

(60) Provisional application No. 61/546,842, filed on Oct. 13, 2011.

(51) Int. Cl.
*G01N 27/327* (2006.01)
*C12Q 1/68* (2006.01)

(52) U.S. Cl.
CPC .......... *G01N 27/3275* (2013.01); *C12Q 1/6804* (2013.01); *C12Q 1/6816* (2013.01); *C12Q 1/6825* (2013.01); *G01N 27/327* (2013.01); *G01N 27/3276* (2013.01)

(58) Field of Classification Search
CPC .......... G01N 27/3275; G01N 27/3276; G01N 27/3277; C12Q 1/6816; C12Q 1/6825
See application file for complete search history.

(56) References Cited

U.S. PATENT DOCUMENTS

| | | |
|---|---|---|
| 5,635,352 A | 6/1997 | Urdea et al. |
| 6,264,825 B1 | 7/2001 | Blackburn et al. |
| 6,350,580 B1 | 2/2002 | Sorge |
| 6,361,944 B1 | 3/2002 | Mirkin et al. |
| 6,417,340 B1 | 7/2002 | Mirkin et al. |
| 6,495,324 B1 | 12/2002 | Mirkin et al. |
| 6,506,564 B1 | 1/2003 | Mirkin et al. |
| 6,582,921 B2 | 6/2003 | Mirkin et al. |
| 6,610,491 B2 | 8/2003 | Mirkin et al. |
| 6,645,721 B2 | 11/2003 | Mirkin et al. |

(Continued)

FOREIGN PATENT DOCUMENTS

| | | |
|---|---|---|
| EP | 1198591 A1 | 4/2002 |
| EP | 1294930 A2 | 3/2003 |

(Continued)

OTHER PUBLICATIONS

Zymek et al., "The Role of Platelet-Derived Growth Factor Signaling in Healing Mycardial Infarcts," Journal of the American College of Cardiology, vol. 48, No. 11, 2006, pp. 2315-2323.*

(Continued)

*Primary Examiner* — Alexander Noguerola
(74) *Attorney, Agent, or Firm* — Thomas Horstemeyer LLP

(57) ABSTRACT

The present disclosure includes an electrochemical proximity assay (ECPA) which leverages two aptamer or antibody-oligonucleotide probes and proximity-dependent DNA hybridization to move a redox active molecule near an electrically conductive base. The ECPA of the present disclosure produces rapid, quantitative results, enabling point-of-care use in the detection of biomarkers of disease.

32 Claims, 16 Drawing Sheets

(56) References Cited

U.S. PATENT DOCUMENTS

| | | | |
|---|---|---|---|
| 6,673,548 B2 | 1/2004 | Mirkin et al. | |
| 6,677,122 B2 | 1/2004 | Mirkin et al. | |
| 6,682,895 B2 | 1/2004 | Mirkin et al. | |
| 6,709,825 B2 | 3/2004 | Mirkin et al. | |
| 6,720,147 B2 | 4/2004 | Mirkin et al. | |
| 6,720,411 B2 | 4/2004 | Mirkin et al. | |
| 6,730,269 B2 | 5/2004 | Mirkin et al. | |
| 6,740,491 B2 | 5/2004 | Mirkin et al. | |
| 6,750,016 B2 | 6/2004 | Mirkin et al. | |
| 6,759,199 B2 | 7/2004 | Mirkin et al. | |
| 6,767,702 B2 | 7/2004 | Mirkin et al. | |
| 6,773,884 B2 | 8/2004 | Mirkin et al. | |
| 6,777,186 B2 | 8/2004 | Mirkin et al. | |
| 6,812,334 B1 | 11/2004 | Mirkin et al. | |
| 6,818,753 B2 | 11/2004 | Mirkin et al. | |
| 6,828,432 B2 | 12/2004 | Mirkin et al. | |
| 6,861,221 B2 | 3/2005 | Mirkin et al. | |
| 6,878,814 B2 | 4/2005 | Mirkin et al. | |
| 6,902,895 B2 | 6/2005 | Mirkin et al. | |
| 6,903,207 B2 | 6/2005 | Mirkin et al. | |
| 6,962,786 B2 | 11/2005 | Mirkin et al. | |
| 6,969,761 B2 | 11/2005 | Mirkin et al. | |
| 6,984,491 B2 | 1/2006 | Mirkin et al. | |
| 6,986,989 B2 | 1/2006 | Mirkin et al. | |
| 7,005,265 B1 | 2/2006 | Fan et al. | |
| 7,098,320 B1 | 8/2006 | Mirkin et al. | |
| 7,169,556 B2 | 1/2007 | Park et al. | |
| 7,208,587 B2 | 4/2007 | Mirkin et al. | |
| 7,250,499 B2 | 7/2007 | Mirkin et al. | |
| 7,259,252 B2 | 8/2007 | Mirkin et al. | |
| 7,291,457 B2 | 11/2007 | Miller et al. | |
| 7,803,542 B2 | 9/2010 | Xiao et al. | |
| 7,807,352 B2 | 10/2010 | Rabbani et al. | |
| 8,003,374 B2 | 8/2011 | Heeger et al. | |
| 2001/0024788 A1* | 9/2001 | Hashimoto | 435/6 |
| 2002/0006617 A1 | 1/2002 | Fan et al. | |
| 2002/0012943 A1 | 1/2002 | Fowlkes et al. | |
| 2002/0172953 A1 | 11/2002 | Mirkin et al. | |
| 2003/0022150 A1* | 1/2003 | Sampson et al. | 435/4 |
| 2003/0054358 A1 | 3/2003 | Mirkin et al. | |
| 2003/0077642 A1* | 4/2003 | Fritsch et al. | 435/6 |
| 2003/0087242 A1 | 5/2003 | Mirkin et al. | |
| 2003/0108922 A1* | 6/2003 | Fritsch et al. | 435/6 |
| 2004/0191801 A1 | 9/2004 | Heeger et al. | |
| 2005/0112605 A1 | 5/2005 | Heeger et al. | |
| 2005/0202449 A1 | 9/2005 | Getts et al. | |
| 2006/0068378 A1 | 3/2006 | Mirkin et al. | |
| 2006/0228703 A1* | 10/2006 | Hartwich et al. | 435/6 |
| 2006/0234253 A1 | 10/2006 | Hasui et al. | |
| 2008/0076139 A1 | 3/2008 | Singh | |
| 2009/0042735 A1 | 2/2009 | Blair et al. | |
| 2009/0305264 A1 | 12/2009 | West et al. | |
| 2009/0325812 A1 | 12/2009 | Mirkin et al. | |
| 2010/0035248 A1 | 2/2010 | Levicky et al. | |
| 2010/0075319 A1 | 3/2010 | Lohse | |
| 2010/0248231 A1 | 9/2010 | Wei et al. | |
| 2010/0297654 A1 | 11/2010 | Heyduk | |
| 2011/0053788 A1 | 3/2011 | Bamdad et al. | |
| 2011/0143955 A1 | 6/2011 | Weiner | |
| 2012/0021426 A1 | 1/2012 | Takoh et al. | |
| 2012/0028242 A1 | 2/2012 | Heyduk et al. | |

FOREIGN PATENT DOCUMENTS

| | | |
|---|---|---|
| EP | 1362121 A2 | 11/2003 |
| EP | 1478774 A2 | 11/2004 |
| EP | 1301625 B1 | 11/2010 |
| WO | 0140511 A2 | 6/2001 |
| WO | 0151665 A2 | 7/2001 |
| WO | 0173123 A2 | 10/2001 |
| WO | 0218643 A2 | 3/2002 |
| WO | 0246472 A2 | 6/2002 |
| WO | 03035829 A2 | 5/2003 |
| WO | 2008001376 A2 | 1/2008 |
| WO | 2011017382 A2 | 2/2011 |
| WO | 2011050069 A1 | 4/2011 |
| WO | 2011161420 A2 | 12/2011 |

OTHER PUBLICATIONS

Sigma-Aldrich web-site published article entitled Self-Assembled Monolayers: Advantages of Pure Alkanethiols, Material Matters 2006, 1.2, 3.*

Silva et al., "Gold electrode modified by self-assembled monolayers of thiols to determine DNA sequences hybridization," J. Chem. Sci., vol. 122, No. 6, Nov. 2010, pp. 911-917.*

Kang et al., Comparing the Properties of Electrochemical-Based DNA Sensors Employing Different Redox Tags, Analytical Chemisty, Nov. 2009, 9109-9113, vol. 81, No. 21, American Chemical Society.

Zhang et al., Electrochemical Aptasensor Based on Proximity-Dependent Surface Hybridization Assay for Protein Detection, Electroanalysis, 2009, 1327-1333, vol. 21, No. 11, Wiley-VCH Verlag GmbH & Co. KGaA, Weinheim.

Zhang et al., Electrochemical Aptasensor Based on Proximity-Dependent Surface Hybridization Assay for Single-Step, Reusable, Sensitive Protein Detection, American Chemical Society, Sep. 2007, 15448-15449, vol. 129, No. 50, JACS Communications.

Fan et al., Electrochemical interrogation of conformational changes as a reagentless method for the sequence-specific detection of DNA, PMAS, Aug. 2003, 9134-9137, vol. 100, No. 16.

Ferapontova et al., An RNA Aptamer-Based Electrochemical Biosensor for Detection of Theophylline in Serum, American Chemical Society, Mar. 2008, 4256-4258, vol. 130, No. 13, JACS Communications.

Li et al., A simple assay to amplify the electrochemical signal by the aptamer based biosensor modified with CdS hollow nanospheres, Biosensors and Bioelectronics, 2011, 3531-3535, vol. 26.

Tong et al., Simply amplified electrochemical aptasensor of Ochratoxin A based on exonuclease-catalyzed target recycling, Biosensors and Bioelectronics, 2011, 97-101, vol. 29.

Hao et al., A Competitor-switched Electrochemical Sensor for Detection of DNA, Chin. J. Chem., 2010, 1978-1982, vol. 28.

Lu et al., Aptamer-based electrochemical sensors that are not based on the target binding-induced conformational change of aptamers, Analyst, 2008, 1256-1260, vol. 133.

Liu et al., Aptamer-based Electrochemical Biosensor for Interferon Gamma Detection, Anal. Chem., Oct. 2010, 8131-8136, vol. 82, No. 19.

Xiao et al., Preparation of electrode-immobilized, redox-modified oligonucleotides for electrochemical DNA and aptamer-based sensing, Nature Protocols, 2007, 2875-2880, vol. 2, No. 11.

Du et al., Multifunctional Label-Free Electrochemical Biosensor Based on an Integrated Aptamer, Anal. Chem., 2008, 5110-5117, vol. 80.

Wu et al., Reusable Electrochemical Sensing Platform for Highly Sensitive Detection of Small Molecules Based on Structure-Switching Signaling Aptamers, Anal. Chem., 2007, 2933-2939, vol. 79.

Deng et al., Sensitive Bifunctional Aptamer-Based Electrochemical Biosensor for Small Molecules and Protein, Anal. Chem., 2009, 9972-9978, vol. 81.

Li et al., Target-Responsive Structural Switching for Nucleic Acid-Based Sensors, Accounts of Chemical Research, 631-641, May 2010, vol. 43, No. 5.

Lin et al., Label-free aptamer-based electrochemical impedance biosensor for 17β-estradiol, Analyst, 2012, 819-822 vol. 137.

* cited by examiner

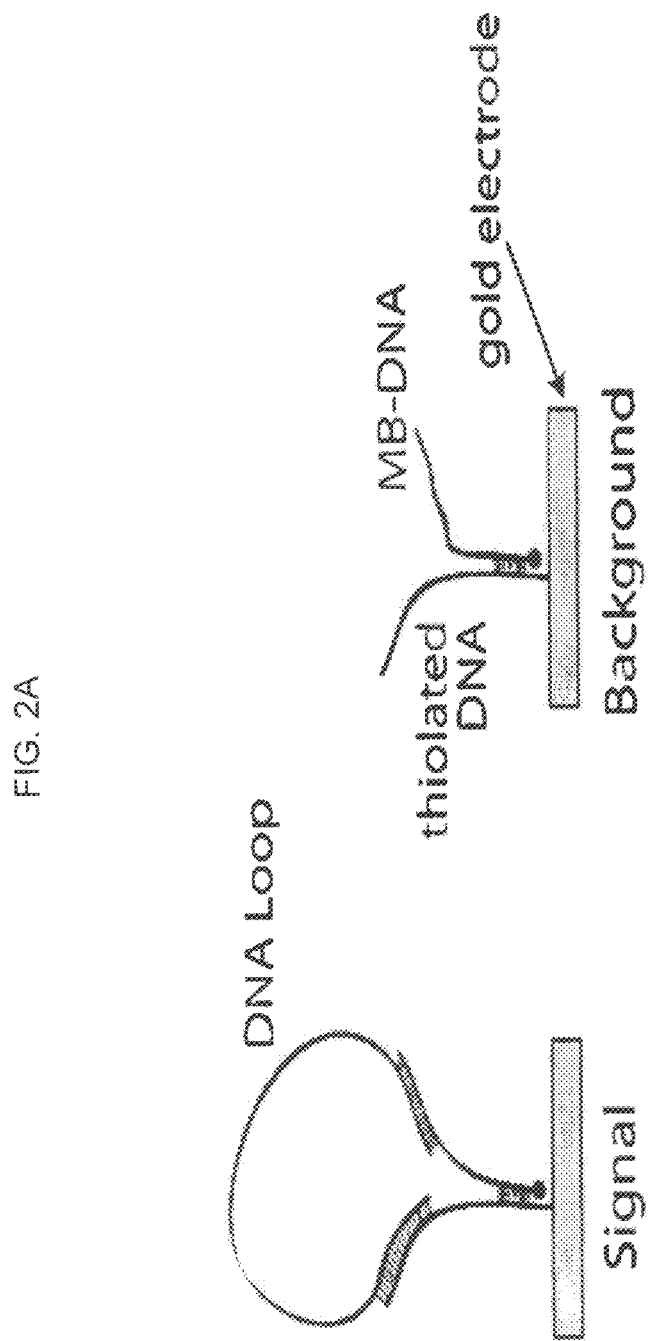

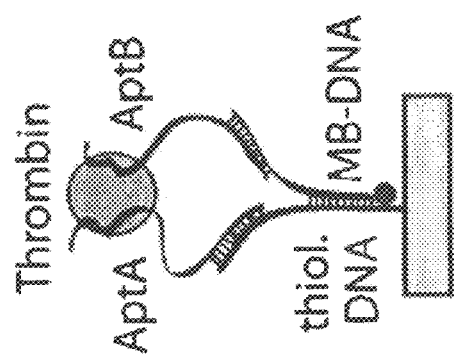

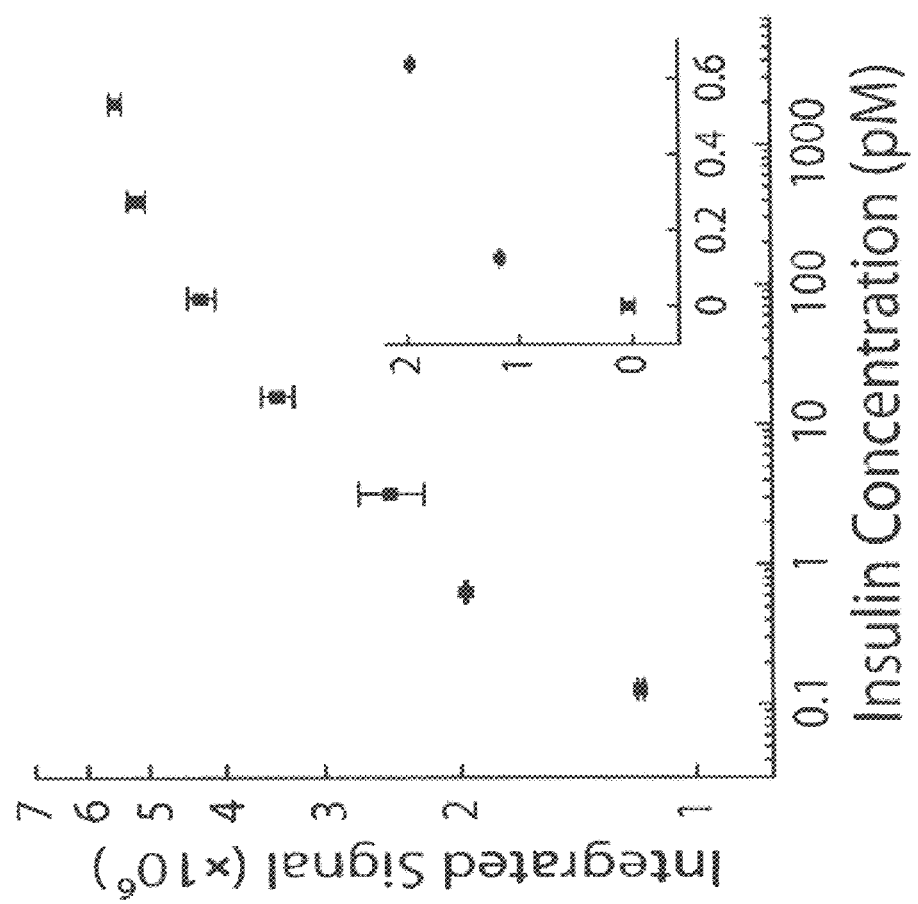

ELECTROCHEMICAL PROXIMITY ASSAY

STATEMENT REGARDING FEDERALLY SPONSORED RESEARCH OR DEVELOPMENT

This invention was made with government support provided by the National Science Foundation, CBET-1067779 (CJE), and by the U.S. Department of Agriculture, 2009-34605-198050 (CS). The government has certain rights in the invention.

CROSS-REFERENCE TO RELATED APPLICATION

This application claims priority to U.S. provisional application entitled "Electrochemical Protein Assay with Background Minimization," having Ser. No. 61/546,842 filed on Oct. 13, 2011, which is entirely incorporated herein by reference.

BACKGROUND

Diagnostics is one of the most critical steps in health care and medical treatment. Specific protein detection is of great importance in this realm, since it is currently one of the predominant methods to diagnose the onset or progression of disease states. Unless specialized point-of-care assays are available for the protein of interest, quantitation is typically performed in a centralized laboratory by technicians. This process is expensive and could waste time that is critical to patient care.

Over the years, clinical approaches for point-of-care testing have addressed this challenge for select analytes, yet these assay formats are highly specialized to the particular target molecule, thus inflexible to apply to other targets. To keep pace with expectations in future point-of-care testing, there is a need for more flexible, yet highly sensitive, quantitative, and easy-to-use methods.

SUMMARY

Embodiments of the present disclosure, in one aspect, relate to an electrochemical proximity assay with background minimization.

Briefly described, embodiments of the present disclosure include an electrochemical proximity assay (ECPA) comprising forming a nucleic acid layer on an electrically conductive base, generating an electrical signal by immersing the electrically conductive base comprising the nucleic acid layer into a solution comprising at least one ECPA probe and at least one target, where the nucleic acid layer, at least one ECPA probe, and at least one target form a complex, and quantifying an amount of the target by analyzing the electrical signal, where the electrical signal changes in proportion to changes in the concentration of the target.

Embodiments of the present disclosure include a method for rapidly detecting, identifying, and/or quantifying a target in a sample comprising mixing a nucleic acid with a competitor DNA, immobilizing the nucleic acid/competitor DNA on an electrically conductive base to form a nucleic acid/competitor DNA layer, mixing the target with at least one molecular recognition element and at least one nucleic acid/electron transfer conjugate to form a probe/target solution, immersing the electrically conductive base comprising the nucleic acid/competitor DNA layer into the probe/target solution to generate an electrical signal, and detecting, identifying, and/or quantifying the target by analyzing the electrical signal, where the electrical signal increases in proportion to the concentration of the target.

Briefly described, embodiments of the present disclosure further include a complex comprising a surface immobilized nucleic acid, a first molecular recognition element, a target, a second molecular recognition element, and a nucleic acid/electron electron transfer conjugate.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 2A-2F illustrate an embodiment of the DNA-based model for ECPA of the present disclosure. FIG. 2A illustrates a continuous DNA Loop used to model the Signal complex shown in FIG. 1. Background is modeled by simply adding MB-DNA without the Loop. FIG. 2B illustrates a depiction of Background reduction. Fewer base pairs (weaker hybridization) between thiolated DNA and MB-DNA results in lower background current. FIG. 2C are graphs that illustrate that both signal and background currents reduced in the voltammograms as the number of base pairs (N) is reduced. At N=5, background is minimized, but signal is reduced significantly. FIG. 2D illustrates a depiction of Background reduction, where a competitor strand prevents or slows Background formation over a given time window. FIG. 2E are graphs that illustrate that the 9-base competitor (C9) was the only one to show baseline current for up to 40 min. FIG. 2F is a graph that illustrates signal and Background voltammograms shown with C9 under optimal conditions, showing more than double the Signal current and equal Background current compared to N=5.

FIGS. 3A-3D illustrate aptamer-based ECPA. FIG. 3A illustrates that with a direct readout, a human thrombin detection limit of about 50 pM is achieved, with a dynamic range up to about 10 nM. FIG. 3B illustrates the principle of an embodiment of the assay of the present disclosure. FIG. 3C is a graph that illustrates example voltammagrams for the blank (lower line) and in the presence of about 2.5 nM thrombin (upper curve). FIG. 3D is a graph that illustrates that the dual-probe assay shows high selectivity with about 93% recovery of signal in the presence of about 2% bovine serum albumin (BSA).

FIGS. 4A-4D illustrate the success of antibody-based ECPA, which greatly improves the flexibility of the assay, since a large variety of protein targets could be quantified this way. FIG. 4A illustrates that insulin as low as about 128 fM was detected with direct readout, with a dynamic range up to about 2 nM. Considering that ECPA does not employ molecular amplification, the measured detection limit of 128 fM and calculated detection limit of 20 fM for insulin are surprisingly low. By comparison, direct fluorescence resonance energy transfer-based proximity assays have reported approximately 1000-fold higher (worse) detection limits for proteins such as insulin. Furthermore, this detection range suitably encompasses the clinical levels of insulin in human blood, from about 50-300 pM. FIG. 4B is an image that illustrates an embodiment of the principle of the assay. FIG. 4C is a graph that illustrates example voltammograms for the blank (lower line) and in the presence of about 2 nM insulin (upper curve). FIG. 4D is a graph that illustrates that the dual-antibody assay also shows high selectivity.

DETAILED DESCRIPTION

Figure 1A:
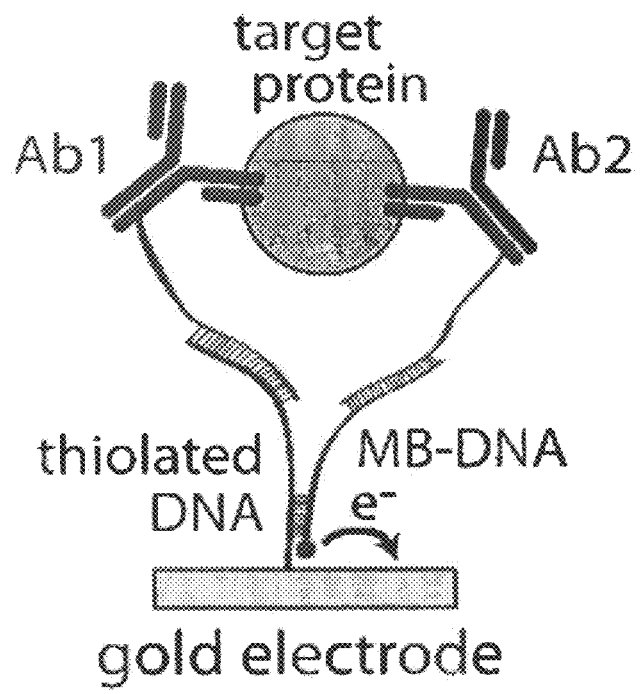
FIGS. 1A-1B illustrate the principle an embodiment of the electrochemical proximity assay (ECPA) of the present disclosure. In the presence of the target protein, this five-part complex moves the redox-active methylene blue (MB) near the gold surface, thus increasing current in proportion to the protein analyte. Depicted here are (FIG. 1A) the final, five-part cooperative complex and (FIG. 1B) the stepwise operation of the assay, in which the electrode with a pre-assembled DNA/competitor monolayer is immersed into a pre-mixed solution of ECPA probes (two Ab-oligos and MB-DNA) and target protein to generate current.
Figure 1B:
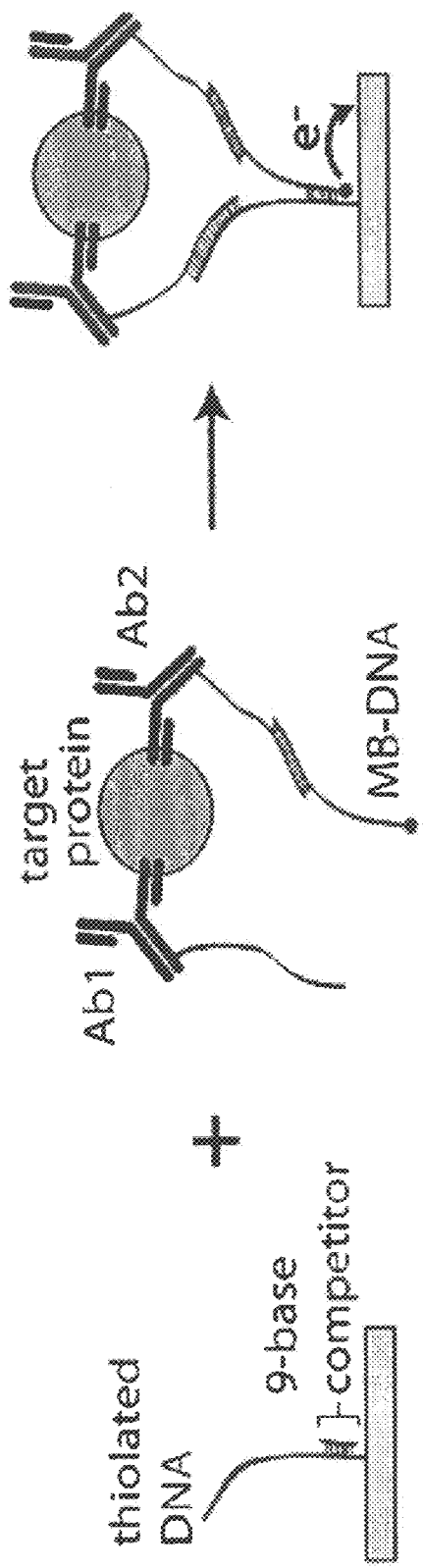

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

As used herein, the terms "antibody" and "antibodies" can include, but are not limited to, monoclonal antibodies, polyclonal/multispecific antibodies, human antibodies, humanized antibodies, camelised antibodies, chimeric antibodies, single-chain Fvs (scFv), single chain antibodies, Fab fragments, F(ab') fragments, disulfide-linked Fvs (sdFv), and anti-idiotypic (anti-Id) antibodies (e.g., anti-Id antibodies to antibodies of the disclosure), and epitope-binding fragments of any of the above. In particular, antibodies include immunoglobulin molecules and immunologically active fragments of immunoglobulin molecules (e.g., molecules that contain an antigen binding site). Immunoglobulin molecules can be of any type (e.g., IgG, IgE, IgM, IgD, IgA and IgY), class (e.g., IgG1, IgG2, IgG3, IgG4, IgA1 and IgA2), or subclass. The antibodies may be from any animal origin including birds and mammals (e.g., human, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes. The antibodies may be monospecific, bispecific, trispecific, or of greater multispecificity.

"Aptamers" may be high affinity, high specificity polypeptide, RNA, or DNA-based probes produced by in vitro selection experiments. Aptamers may be generated from random sequences of nucleotides or amino acids, selectively screened by absorption to molecular antigens or cells, and enriched to purify specific high affinity binding ligands, for example. In solution, aptamers may be unstructured but may fold and enwrap target epitopes providing specific binding recognition. The unique folding of the nucleic acids around the epitope, for example, affords discriminatory intermolecular contacts through hydrogen bonding, electrostatic interaction, stacking, and shape complementarity.

Aptamers must also be differentiated from the naturally occurring nucleic acid sequences that bind to certain proteins. These latter sequences generally are naturally occurring sequences embedded within the genome of the organism that bind to a specialized sub-group of proteins or polypeptides, or their derivatives, that are involved in the transcription, translation, and transportation of naturally occurring nucleic acids, i.e., protein-binding nucleic acids. Aptamers on the other hand are short, isolated, non-naturally occurring nucleic acid molecules. While aptamers can be identified that bind nucleic acid-binding proteins, in most cases such aptamers have little or no sequence identity to the sequences recognized by the nucleic acid-binding proteins in nature. More importantly, aptamers can be selected to bind virtually any protein (not just nucleic acid-binding proteins) as well as almost any target of interest including small molecules, carbohydrates, peptides, etc. For most targets, even proteins, a naturally occurring nucleic acid sequence to which it binds does not exist. For those targets that do have such a sequence, i.e., nucleic acid-binding proteins, such sequences will differ from aptamers as a result of the relatively low binding affinity used in nature as compared to tightly binding aptamers. Aptamers are capable of specifically binding to selected targets and modulating the target's activity or binding interactions, e.g., through binding, aptamers may block their target's ability to function. The functional property of specific binding to a target is an inherent property of an aptamer. Proximity assays, such as the method described herein, are capable of functioning with any molecular recognition elements, which includes aptamers, nucleic acid binding proteins, antibodies, etc.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above. The term "DNA molecule" includes nucleic acids/polynucleotides that are made of DNA.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein.

Discussion

Embodiments of the present disclosure include an electrochemical assay that provides for a highly sensitive and selective quantitation of a variety of targets (e.g., target proteins). The present disclosure includes an electrochemical proximity assay (ECPA) which leverages two aptamer or antibody-oligonucleotide probes and proximity-dependent DNA hybridization to move a redox active molecule near an electrically conductive base. The ECPA of the present disclosure produces rapid, quantitative results (e.g., five minutes or less), enabling point-of-care use in the detection of biomarkers of disease.

Embodiments of the present disclosure include an electrochemical proximity assay (ECPA) comprising forming a nucleic acid layer on an electrically conductive base (substrate), generating an electrical signal by immersing the electrically conductive base comprising the nucleic acid layer into a solution comprising at least one ECPA probe and at least one target, where the nucleic acid layer, at least one ECPA probe, and at least one target form a complex, and quantifying an amount of the target by analyzing the electrical signal, wherein the electrical signal changes (e.g., increases or decreases) in proportion to changes in the concentration of the target. In an embodiment, the nucleic acid layer comprises at least one surface immobilized nucleic acid strand (e.g., surface immobilized DNA strand). In another embodiment, the surface immobilized DNA is selected from a thiolated DNA, an amine labeled DNA, an RNA, a modified RNA, and a combination thereof. Surprisingly, even though ECPA is a direct measurement technique without molecular amplification, results have shown that protein concentration detection limits at least at the low femtomolar level can be achieved. Thus, ECPA is capable of outperforming any currently known protein quantitation technique.

Embodiments of the present disclosure include an ECPA where the surface immobilized DNA comprises thiolated DNA that forms a self-assembled monolayer (SAM) on an electrically conductive base (e.g., a gold electrode). In an embodiment, the self-assembly of thiolated DNA strands onto the electrically conductive base is accomplished via the alkanethiol moiety at the 5' terminus.

Embodiments of the present disclosure further include an ECPA where the nucleic acid layer is formed by covalent attachment of the nucleic acid to the electrically conductive base. In an embodiment, the electrically conductive base (substrate) is selected from, but not limited to, a metal electrode (e.g., gold, platinum), an activated carbon electrode, a conductive ceramic, a conductive glass, and any combination thereof.

Embodiments of the present disclosure include an ECPA where the ECPA probe comprises at least one molecular recognition element specific to the target and at least one nucleic acid/electron transfer conjugate. In an embodiment, the electron transfer element (e.g., oxidized or reduced) is any electrochemically active molecule, for example, but not limited to, methylene blue (MB), ferrocene/ferricinium, tris(2-2'-bipyridine)Ru(II), quinone/hydroquinone, and their derivatives, and any combination thereof.

Embodiments of the present disclosure include an ECPA where the molecular recognition element is selected from an aptamer, an antibody, an antibody/DNA conjugate, and a combination thereof.

Embodiments of the present disclosure include an ECPA where the nucleic acid layer further comprises at least one short single stranded nucleic acid competitor (e.g., a short single stranded DNA competitor). In an embodiment, the nucleic acid competitor has complimentary bases with the surface immobilized nucleic acid. In another embodiment, the nucleic acid competitor has 5 to 50 complimentary bases with the surface immobilized nucleic acid. In yet another embodiment, the nucleic acid competitor has complimentary bases with the surface immobilized nucleic acid including, but not limited to, 1 to 20 complimentary bases, 1 to 50 complimentary bases, 1-100 complimentary bases, 5 to 20 complimentary bases, 5 to 100 complimentary bases, and 9 complimentary bases. Generally speaking, such a competitor approach could be utilized in a variety of proximity ligation assays.

Embodiments of the present disclosure include an ECPA where the competitor nucleic acid impedes the hybridization of the nucleic acid/electron transfer conjugate.

Embodiments of the present disclosure include an ECPA with background minimization. Signal enhancement over background in ECPA is based on the proximity effect, i.e., the marked increase in the effective concentrations of the ECPA probe and nucleic acid due to simultaneous binding of the two probes to the same target (e.g., protein). This allows the ECPA probe/nucleic acid interaction to be weak in the absence of target ("background") yet strong in the presence of target ("signal").

Embodiments of the present disclosure include an ECPA for identifying, detecting, and/or quantifying a target in a sample where the target is selected from a protein, a small molecule, a multi-protein complex, a nucleic acid, a polymer, a whole cell, a virus, a biological polymer, and a combination thereof. In an embodiment, the target causes the nucleic acid/electron transfer conjugate to move closer to a surface of the electrically conductive base, replacing the competitor nucleic acid, and allowing an electron transfer process. In another embodiment, multiple targets are detected and/or quantified simultaneously.

Embodiments of the present disclosure include an ECPA where the complex is re-usable. In an embodiment, the complex is used for measurement, then washed with a solvent so that the complex is re-useable. In another embodiment, the complex is washed with a DNA competitor strand, where the DNA competitor strand displaces the previously immobilized ECPA probe.

Embodiments of the present disclosure include an ECPA where detection and/or quantification of the target is used in the detection and/or treatment of health related issues including, but not limited to, heart attack, stroke, rhabdomylosis, fertility, diabetes, obesity, metabolic syndrome, sepsis, inflammatory response, food safety, tuberculosis, and any combination thereof. In an embodiment, the ECPA is used to detect and/or treat any disease and/or condition diagnosed by a protein or peptide.

Embodiments of the present disclosure include a method for rapidly detecting, identifying, and/or quantifying a target in a sample comprising mixing a nucleic acid with a competitor DNA, immobilizing the nucleic acid/competitor DNA on an electrically conductive base to form a nucleic acid/competitor DNA layer, mixing the target with at least one molecular recognition element and at least one nucleic acid/electron transfer conjugate to form a probe/target solution, immersing the electrically conductive base comprising the nucleic acid/competitor DNA layer into the probe/target solution to generate an electrical signal; and detecting, identifying, and/or quantifying the target by analyzing the electrical signal, where the electrical signal changes (e.g., increases or decreases) in proportion to the concentration of the target. In an embodiment, the first two steps of the method disclosed are performed in any order in relation to each other or simultaneously. This electrical signal change provides means to detect or quantify the target, and the high specificity of the ECPA probes provide means to identify the target, even in the presence of complex backgrounds such as blood or urine.

In an embodiment of the present disclosure, the sample comprises a biological sample selected from the group consisting of: blood serum, whole blood, nasal aspirates, saliva, urine, feces, cell lysate, dialysis sampling, tissue biopsy, cell media, and a combination thereof. In another embodiment, the biological sample is unprocessed. For example, whole blood, saliva, or urine samples that have not been processed through dilution or purification steps. In another embodiment, the method is used in a basic research laboratory to detect, quantify, or identify proteins, peptides, or cells. In another embodiment, the method is used in a clinical laboratory to detect, quantify, and/or identify biomarkers of disease. In yet another embodiment, the method is used at the point-of-care (POC) to detect, quantify, and/or identify biomarkers of disease.

Embodiments of the present disclosure include a method of detecting, identifying, and/or quantifying a single molecule of the target or a concentration of the target as low as the attomolar to millimolar range. In an embodiment, a concentration of a target in the sample as low as about 1 attomolar is detected. In an embodiment, the method is used to detect a single molecule of the target protein or peptide. In another embodiment, the method is used to detect femtomolar concentrations of the target. In another embodiment, the method is used to detect picomolar concentrations of the target. In another embodiment, the method is used to detect nanomolar concentrations of the target. In another embodiment, the method is used to detect micromolar concentrations of the target. In another embodiment, the method is used to detect millimolar concentrations of the target.

Embodiments of the present disclosure include a method of detecting a target in a sample where the target is quantified using a readout method selected from surface plasmon resonance (SPR), Raman spectroscopy, and a combination thereof.

Embodiments of the present disclosure include a complex comprising a surface immobilized nucleic acid, a first molecular recognition element, a target, a second molecular recognition element, and a nucleic acid/electron transfer conjugate. In an embodiment, the surface immobilized nucleic acid is covalently attached to an electrically conductive base, the first and second molecular recognition elements are specific to and bound to the target, and the complex comprises a circular structure on the electrically conductive base through proximity dependent hybridization of the surface immobilized nucleic acid and the nucleic acid/electron transfer conjugate.

In an embodiment, the nucleic acid comprises surface immobilized DNA. In an embodiment, the nucleic acid/electron transfer conjugate comprises a methylene blue conjugated DNA (MB-DNA).

Embodiments of the present disclosure include a complex where the first and second molecular recognition elements are each independently selected from an aptamer, an antibody, an antibody/DNA conjugate, and a combination thereof.

Embodiments of the present disclosure include a complex where the target is selected from a peptide, a protein, a small molecule, a whole cell, a multi-protein complex, a nucleic acid, a virus, and a combination thereof.

Embodiments of the present disclosure include a complex where the complex comprises a circular structure on an electrically conductive base through proximity dependent hybridization of the surface immobilized DNA and the DNA/electron transfer conjugate. In an embodiment, the complex further comprises at least one short single stranded nucleic acid competitor to the surface immobilized nucleic acid, where the nucleic acid competitor has complimentary bases with the nucleic acid.

EXAMPLES

Introduction

The present disclosure includes examples of an electrochemical proximity assay (ECPA), which leverages two aptamer or antibody-oligonucleotide probes and proximity-dependent DNA hybridization to move a redox active molecule near a gold electrode. A DNA-based experimental model was used to optimize the assay format, and aptamer- and antibody-based ECPA were shown functional with high sensitivities and low detection limits, employing a short DNA competitor to limit background current. This background-reduced ECPA was shown to match or outperform currently used ELISA kits for insulin detection.

Of particular importance is the proof-of-concept provided by antibody-based ECPA. ECPA performs well in quantifying any protein with an available antibody pair. Combining the assay's flexibility and high sensitivity with the simplicity of direct electrochemical readout, ECPA will be useful in a variety of settings in the future, including but not limited to medical diagnostics, biological research, and point-of-care testing.

Diagnostics is one of the most critical steps in health care and medical treatment. Specific protein detection is of great importance in this realm, since it is currently one of the predominant methods to diagnose the onset or progression of disease states. Unless specialized point-of-care assays are available for the protein of interest, quantitation is typically performed in a centralized laboratory by technicians. This process is expensive and could waste time that is critical to patient care. Over the years, clinical approaches for point-of-care testing have addressed this challenge for select analytes, yet these assay formats are highly specialized to the particular target molecule, thus inflexible to apply to other targets. To keep pace with expectations in future point-of-care testing, there is a need for more flexible, yet highly sensitive, quantitative, and easy-to-use methods.

Although point-of-care devices are welcome in clinical and research laboratories, the existence of surrounding infrastructure places fewer constraints on methodology. Based on their inherent flexibility, sandwich enzyme-linked immunosorbent assays (ELISA) have emerged as the method of choice for protein quantitation in clinical and research laboratories. Unfortunately, these heterogeneous assays require expert users with dedicated instrumentation, and they are time-consuming, laborious, and expensive. Quantitative, point-of-care protein analysis is thus not possible with standard sandwich ELISA formats. Nonetheless, the flexibility of the dual-antibody recognition concept is highly valuable and has served as a guide to various alternative strategies in recent years.

Proximity immunoassays such as the proximity ligation assay (PLA) or the molecular pincer assay can overcome some of the limitations of ELISA. PLA, for example, is one of the most simple-to-use and sensitive protein assays developed to date. The assay is homogeneous (no washing steps), and detection limits rival or outperform ELISAs, even with much smaller sample volumes. A key concept in PLA is the "proximity effect," which relies on simultaneous recognition of a target molecule by a pair of affinity probes. The bound probes can then be covalently linked by enzymatic ligation of their oligonucleotide tails, and qPCR is used as the readout, with products proportional to target protein concentration. PLA has been shown functional with aptamer pairs and with a variety of antibody pairs. Proximity assays can also employ antibody-oligonucleotide conjugates as probes, since the popularity and success of sandwich methodology (ELISA, Western blots) has afforded a large, commercially available library of antibody pairs against many proteins. These assays thus provide simpler and less expensive alternatives to ELISA.

Nonetheless, limitations in current proximity assays impede their use in a point-of-care setting. Although the use of qPCR gives PLA its high sensitivity, this readout requires that each sample be added to a tube with ligation and PCR reagents, and then be inserted into a qPCR instrument followed by 1-2 hours of amplification and analysis. The molecular pincer assays are simpler and more rapid (<20 min), making them more amenable to point-of-care measurements by fluorescence readout; however, the limit of detection of these assays is several orders of magnitude higher than PLA. Thus, there is a need for a more sensitive yet simpler readout for proximity assays that is amenable to point-of-care testing.

Electrochemical detection is of particular interest in the development of biosensors because it offers great signal stability, simple instrumentation, high sensitivity, and ease of calibration compared to fluorescence, as well as excellent compatibility with miniaturization technologies. The present disclosure includes the marriage of the proximity assay concept with electrochemical detection to give a simple, highly sensitive, flexible strategy for specific protein quantitation, termed the electrochemical proximity assay (ECPA). ECPA uses the proximity effect to move an electrochemically active label, methylene blue (MB), closer to a gold electrode upon binding of two probes to a protein target, an approach akin to electrochemical DNA sensing or specialized aptamer-based protein sensing. In the presence of protein targets, the redox current in ECPA is quantified using an electrochemical technique such as square wave voltammetry (SWV) and is found to depend directly on the concentration of target. Embodiments of the present disclosure use a DNA-based experimental model to optimize signal-to-background ratios, ultimately providing a direct insulin detection limit that is lower than most commercially available ELISAs, with a dynamic range >40-fold wider than these ELISAs. These results were achieved with direct electrochemical readout, i.e., without requiring washing steps, which bodes well for the future of ECPA in point-of-care settings. In contrast to other approaches for electrochemical protein sensing, ECPA should be useful for any protein with available antibody pairs or similar molecular recognition elements.

Experimental Design

Reagents and Materials. All solutions were prepared with deionized, ultra-filtered water (Fisher Scientific). The following reagents were used as received: insulin antibodies (clones 3A6 & 8E2; Fitzgerald Industries), 4-(2-hydroxyethyl)-1-piperazineethanesulfonic acid (HEPES) (99.5%), tris-(2-carboxyethyl)phosphine hydrochloride (TCEP), (Sigma-Aldrich, St. Louis, Mo.), bovine serum albumin (BSA, 98%; EMD Chemicals Inc), human thrombin, immunoglobulin E (IgE), and insulin (Sigma Aldrich). Methylene blue-conjugated DNA (MB-DNA) was purchased from Biosearch Technologies (Novato, Calif.), purified by RP-HPLC. Oligonucleotides were obtained from Integrated DNA Technologies (IDT; Coralville, Iowa), with purity and yield confirmed by mass spectrometry and HPLC, respectively. Sequences (listed 5' to 3') for aptamer based ECPA were as follows.

Thrombin aptamer A (THRaptA): AGTCCGTGGTAG-GGCAGGTTGGGGTGACTTTTTTTTTTTTTTTTATA-TTTTTTTTTTCTCGCGGATTTGAACCCTAACG (SEQ. ID No. 1); Thrombin aptamer B (THRaptB): TAGGAAAAG-GAGGAGGGTGGGATTGGTGTGTGTTTTTTTTTTTTT-TTTTTTTTTTTTTTTTTTTGGTTGGTGTGGTTGG (SEQ. ID No. 2). Sequences (listed 5' to 3') for antibody-based ECPA were as follows. Insulin antibody arm 1 (AbArm1):/5AmMC6//iSp18/CCCACTTAAACCTCAAT-CCACGCGGATTTGAACCCTAACG (SEQ. ID No. 3); Insulin antibody arm 2 (AbArm2): TAGGAAAAGGAGG AGGGTGGCCCACTTAAACCTCAATCCA/iSp18//3Am MC6/(SEQ. ID No. 4).

Preparation of the Electrode and DNA Monolayer Assembly. ECPA sensors for the model system, for thrombin detection, and for insulin detection were fabricated using a gold working electrode (Bioanalytical Systems Inc., r=0.75 mm). The gold electrode was polished carefully to a mirror surface with an aqueous slurry of 0.05 µm diameter alumina particles and then successively washed in an ultrasonic cleaner with water. The electrode was then immersed into fresh piranha solution ($H_2SO_4/H_2O_2$, 3:1) for 5 minutes, rinsed with D. I. water, and dried under a stream of nitrogen gas. (Caution: piranha solution is dangerous to human health and should be used with extreme caution and handled only in small quantities). Finally, the gold electrode was electrochemically polished by scanning the potential from −0.5 to 1.5 V in 0.1 M $H_2SO_4$ at a scan rate of 0.1 V s$^{-1}$ for 50 cycles. The cleaned gold electrode was thoroughly washed with D. I. water and ethanol and dried under flowing nitrogen.

Prior to modification of the electrode, 1 µL of 200 µM thiolated-DNA and 1 µL of 200 µM MB-DNA were each separately mixed with 2 µL of 10 mM TCEP in two 200-µL PCR tubes. These tubes were incubated for 90 min at room temperature (21° C.) for reduction of disulfide bonds in the thiolated-DNA and to reduce the MB-moiety of the MB-DNA. Both of these solutions were then diluted to a total volume of 200 µL in HEPES/NaClO$_4$ buffer (10 mM HEPES and 0.5 M NaClO$_4$, pH 7.0) to a final concentration of 1 µM. Unless otherwise noted, all solutions used in the experiments to follow were carried out at pH 7.0. For immobilization, the previously cleaned gold electrode was transferred directly to the diluted and reduced thiolated-DNA solution and incubated for 16 h at room temperature in the dark. Following the formation of a self-assembled monolayer (SAM), excess thiolated-DNA physically adsorbed on the electrode surface was removed via a room temperature-deionized water rinse (~20 s). For all assay strategies employing the competitor DNA strands (most formats listed below), this same process was followed, except after reduction by 10 mM TCEP, the reduced thiolated-DNA solution was diluted to a total volume of 200 µL in HEPES/NaClO$_4$ buffer and incubated with 2 µM competitor DNA sequence (C9) for 60 min at room temperature in the dark. For immobilization in competitor systems, the cleaned gold electrode was transferred directly to this equilibrated thiolated-DNA/competitor solution then incubated for 16 h at room temperature in the dark.

ECPA Probe Assembly and Electrochemical Measurements. Electrochemical measurements were performed using an Epsilon electrochemistry workstation (Bioanalytical Systems, Inc.) with a standard three-electrode configuration including a Ag|AgCl(s)|KCl(sat) reference electrode (Bioanalytical Systems, Inc.), a homemade platinum gauze flag (0.77 cm$^2$) counter electrode, and a gold working electrode. All potentials are reported relative to the saturated Ag|AgCl reference electrode. Electrochemical measurements were performed in HEPES/NaClO$_4$ buffer using square wave voltammetry (SWV) with a 50 mV amplitude signal at a frequency of 60 Hz, over the range from −0.45 V to 0.00 V versus Ag|AgCl reference. The characteristic voltammetric peak of MB was detected by SWV at −210 mV (vs Ag/AgCl). MB was chosen as the redox tag due to its excellent shelf life and robust electrochemical response in serum compared to other redox tags, such as ferrocene. The electrochemical response of each sensor was measured as follows: (1) reference and measurement SWV data sets were collected; (2) both raw data sets were smoothed using a 21-point boxcar function and baseline corrected (all data corrected with B-spline generated baseline in Origin 8 using two regions: −0.40 V to −0.35 V and −0.08 V to 0.00 V); and (3) difference traces were generated. Signal (with target) and Background (no target) voltammograms were treated in this manner and are presented as difference traces. To prepare calibration graphs and calculate standard deviations, traces were integrated from −0.330 to −0.100 V. In the case of the aptamer-based system, we report the average of three measurements, while in the case of the antibody-based system the average of two measurements is reported.

Model System Strategy 1—Decreasing binding affinity by reducing the number of complementary bases. The electrode was modified as described above and was placed into a glass electrochemical cell with HEPES/NaClO$_4$ buffer. Three different thiolated DNA sequences, G5, G7, and G10 (Table 1), were used in Strategy 1 of the model system. In this way, the affinity of thiolated DNA and MB-DNA were adjusted through changes in the number of complementary bases between them. For modeling signal, the sensor was immersed in 10 nM ECPA-loop and 15 nM MB conjugated DNA sequences in 3 mL HEPES/NaClO$_4$ buffer. For modeling background, the sensor was immersed in 15 nM MB conjugated DNA in 3 ml HEPES/NaClO$_4$ buffer. Both signal and background currents were measured at the 15-min time point.

Model System Strategy 2—Use of a short DNA competitor. The electrode was modified as described above and was placed into a glass electrochemical cell with HEPES/NaClO$_4$ buffer. Three different competitor DNA sequences, C7, C8, and C9, were used in Strategy 2 of the model system (Table 1). The sensor was allowed to equilibrate in 3 ml HEPES/NaClO$_4$ buffer with various concentrations of competitors for 6 h. For modeling background in the competitor systems, redox current was measured at each 10 min of the first hour, then at 90 and 120 min. Once C9 was chosen, 1:3, 1:7, 1:10, and 1:25 molar ratios of MB-DNA:C9 were tested at a fixed concentration of 15 nM MB-DNA.

Preparation of antibody-oligonucleotide conjugates. The antibody-oligonucleotide conjugates used in the insulin ECPA, AbArm1-3A6 and AbArm2-8E2, were prepared by conjugating AbArm1 to insulin antibody 3A6 ($K_d \approx 1$ nM) and AbArm2 to insulin antibody 8E2 ($K_d \approx 0.1$ nM), respectively (antibodies obtained from Fitzgerald Industries). Conjugation reactions and purification steps were accomplished using an Antibody-Oligonucleotide All-In-One Conjugation Kit (Solulink), according to the manufacturer's instructions. Briefly, the oligonucleotides were first activated with sulfo-S-4FB, and their quantities and qualities were confirmed using absorbance, specifically $A_{260\ nm}$ of unmodified activated oligonucleotides and the $A_{260\ nm}$ to $A_{360\ nm}$ ratio after the modification of activated oligonucleotides. Antibodies were also activated with S-HyNic. Activated oligonucleotides and antibodies were then mixed and incubated at room temperature for 2 h. Once the conjugation reaction was stopped, conjugates were further purified using the supplied magnetic affinity matrix. The final concentrations of the conjugates were determined by the Bradford protein assay. AbArm1-

3A6 and AbArm2-8E2 were synthesized with 45% and 86% recovery from the initial amount of antibodies (100 µg).

Example 1

In this example, a model system is described which allows optimization of conditions for ECPA. The principle of the electrochemical proximity assay (ECPA) is shown in FIG. 1A. The sensor is prepared by self-assembly of thiolated DNA strands onto a gold electrode via the alkanethiol moiety at the 5' terminus. The quantitative capacity of ECPA stems from cooperative hybridization of the five-part complex shown in FIG. 1A: thiolated DNA—DNA conjugated antibody 1—target protein—DNA conjugated antibody 2—MB conjugated DNA. The five-part complex forms a circular structure on the sensor surface through proximity-dependent hybridization of the thiolated DNA and MB-DNA, which is the step that brings MB close enough to the gold electrode surface for electrochemical current enhancement. This process results in a quantity of electrons transferred from MB to the electrode that is proportional to the original amount of protein analyte ("signal"), albeit with some analyte-independent current generated by hybridization of thiolated DNA and MB-DNA only ("background"). Although voltammetry or amperometry does not differentiate signal and background currents, under optimized conditions, the signal will greatly exceed the background to allow highly sensitive, direct electrochemical quantitation of the protein analyte. Similar to what has been observed in PLA or the molecular pincer assays, signal enhancement over background in ECPA is based on the proximity effect; that is, the marked increase in the effective concentrations of the MB-DNA and thiolated DNA due to the simultaneous binding of the two probes to the same protein. This allows the MB-DNA/thiolated DNA interaction to be weak in the absence of protein ("background") yet strong in the presence of the protein ("signal"). Finally, it should be noted that the detection limits of proximity assays are often well below the $K_d$ values of the individual probes, which can be attributed to the chelate-like effect of utilizing two probes in a cooperative fashion, often termed the "proximity effect."

Through binding equilibria, a fraction of thiolated DNA will always hybridize with the MB-DNA sequences, even in the absence of target analyte, resulting in target-independent hybridization, recruitment of MB to the gold surface, and an increase in current. Without being bound by any particular theory, a portion of this background current could also result from non-specific adsorption of MB-DNA to the surface, although the results suggest that specific binding is the major cause. The presence of this background current is obviously detrimental to the assay. Two strategies were applied in attempt to lower the background using the model system, as discussed below.

DNA-Based Experimental Model of ECPA. The present disclosure utilizes a DNA loop to model the probe-target complex in ECPA (FIG. 2A), making the assumption that probe affinity for the target protein is infinite. The 80-nucleotide DNA loop mimics formation of the ECPA complex, bringing the electron donor (MB) near the gold surface and increasing redox current. Background was modeled using only the thiolated DNA and MB-DNA (FIG. 2A). This experimental model greatly simplified the optimization of experimental parameters. Since the surface-dependent ECPA involves a different type of cooperative complex formation compared to homogeneous PLA, two strategies were devised for minimizing background in ECPA.

Figure 2B:
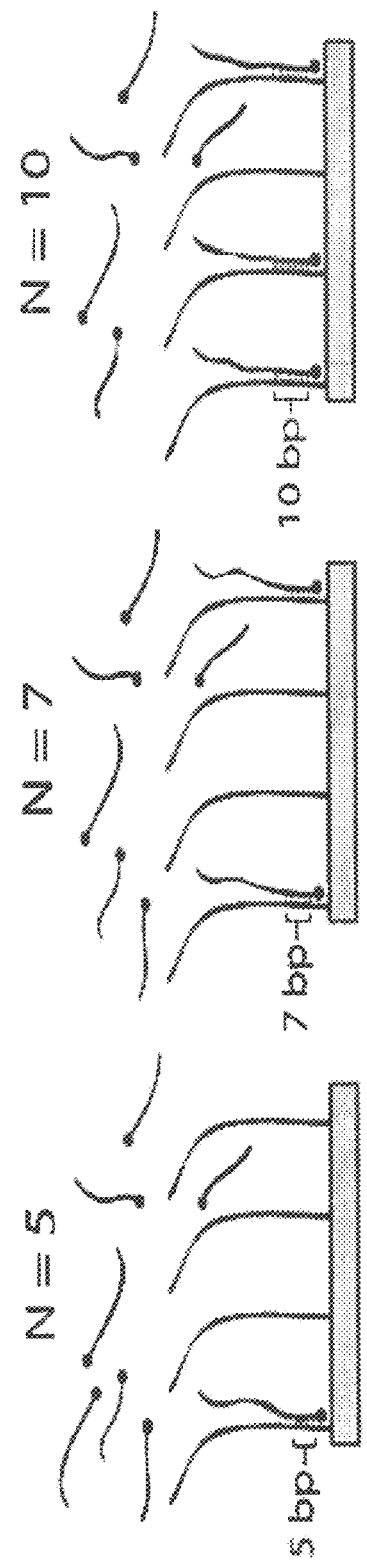
Figure 2C:
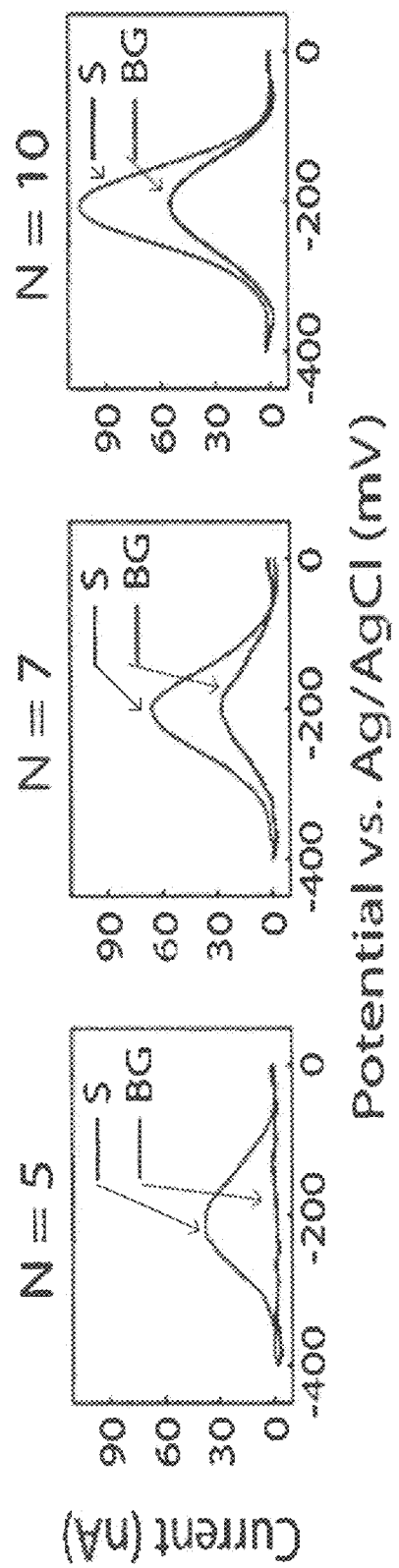

The first strategy was to decrease the binding affinity between thiolated DNA and MB-DNA by reducing the number of complementary bases in the thiolated DNA (FIG. 2B). The hypothesis was that the amount of background hybridization between thiolated DNA and MB-DNA would be greatly reduced, thereby reducing background current greatly without a large decrease in signal current. FIG. 2C compares the signal and background responses of the system with 5, 7, and 10 complimentary bases (G5, G7, and G10 strands). Comparing G10 to G7, as hypothesized, the background current was reduced by 2-fold while signal current was reduced by only 1.6-fold. Furthermore, compared to a background peak current of 54 nA with G10, it was indeed possible to reduce the background current to baseline using G5. However, the background reduction was accompanied by a large decrease in signal peak current from 104 nA down to 38 nA, since the weakened connection also weakened hybridization of the DNA Loop (model of signal). One advantage of the G5 system, however, is the rapid generation of signal. Signal was observed in as little as one minute from immersion of the electrode into the solution.

Figure 2D:
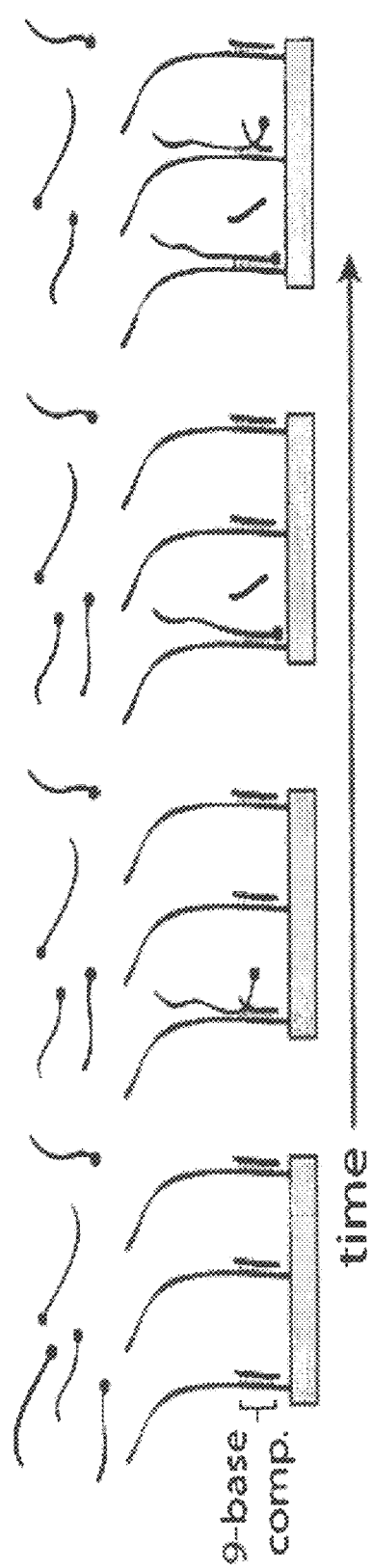
Figure 2E:
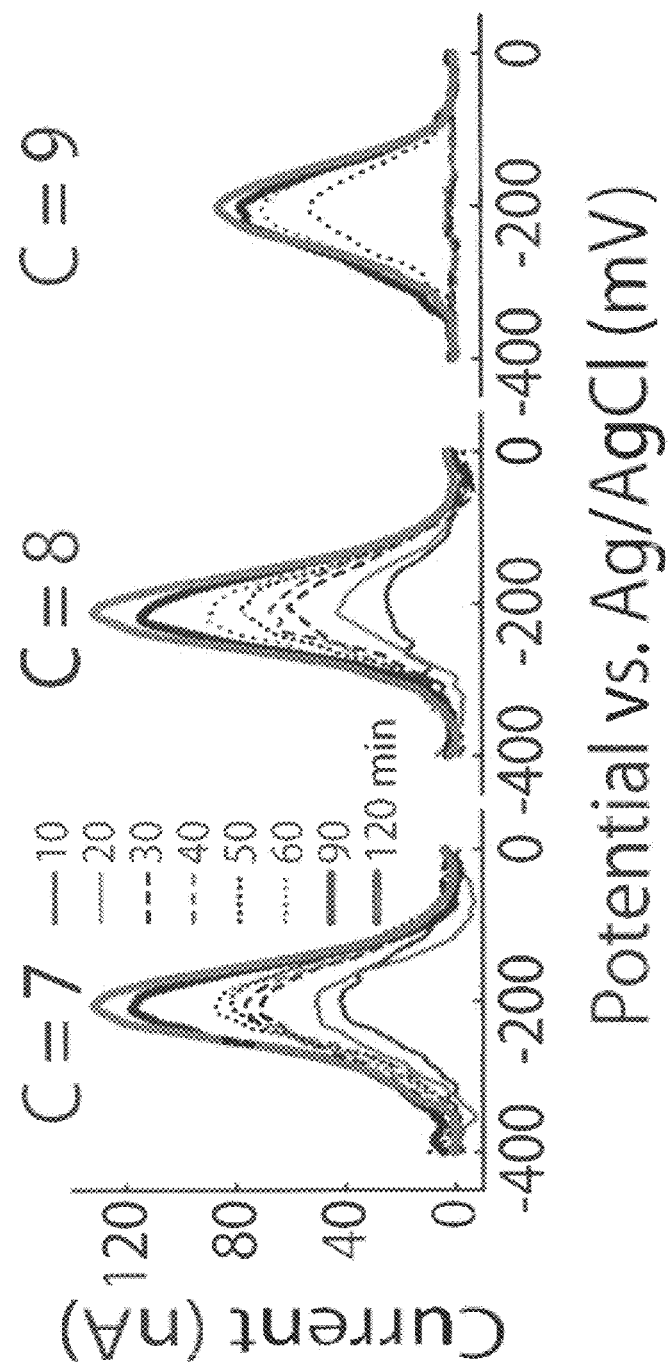
Figure 2F:
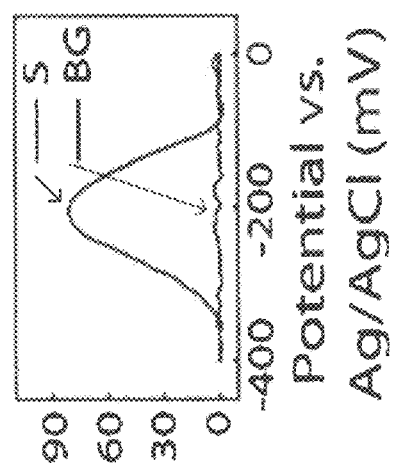

In an attempt to reduce background without such a large signal reduction, the second strategy was to utilize a short DNA competitor with the G10 system. It was hypothesized that when using a competitor sequence, background hybridization would occur more slowly than signal hybridization, since both signal and background complexes must displace the short competitor prior to current enhancement by the MB-DNA strand. FIG. 2D shows a representation of the delayed background formation over time, mediated by competition with competitor strands. This way, signal of similar magnitude to that in the N=10 case above should form rapidly, while background would be delayed kinetically by the competitor. FIG. 2E shows signal and background responses of the system with 7-, 8-, and 9-base competitors (C7, C8, and C9). As hypothesized, the hybridized competitor sequences blocked access of MB-DNA to the thiolated DNA, thereby slowing background formation. FIG. 2E shows that with C7 and C8, background currents of 47 and 24 nA were detected even 10 min after addition of MB-DNA, while no background was detected for as long as 40 min using C9. Since C9 allowed a 40-min time window for detection, C9 was chosen as the competitor for further experiments. Upon addition of the Loop (model of signal), significant signal current of 81 nA was possible after 40 min, while C9 prevented background formation (FIG. 2F). One example of optimal conditions were 15 nM MB-DNA and 100 nM C9, which were applied in the aptamer-based ECPA system.

Example 2

The present disclosure includes a separation-free, electrochemical assay format with direct readout that is amenable to highly sensitive and selective quantitation of a wide variety of target proteins. The first generation of the electrochemical proximity assay (ECPA) is composed of two thrombin aptamers which form a cooperative complex only in the presence of target molecules, moving a methylene blue (MB)-conjugated oligonucleotide close to a gold electrode. Without washing steps, electrical current is increased in proportion to the concentration of a specific target protein. By employing a DNA-based experimental model with the aptamer system, the present disclosure illustrates that addition of a short DNA competitor reduces background current of the MB peak to baseline levels. As such, the detection limit of aptamer-based ECPA for human thrombin is about 50 pM via direct readout.

The dual-probe nature of ECPA gives high selectivity and 93% recovery of signal from 2.5 nM thrombin in 2% bovine serum albumin (BSA).

For the aptamer-based ECPA system, the sensor was allowed to equilibrate in 3 ml HEPES/NaClO$_4$ buffer with 100 nM C9 for 6 h. Thrombin aptamers (THRaptA and THRaptB) were first folded by heating to 95° C. and cooled rapidly by immersion in ice water to promote intramolecular interactions. Thrombin of various concentrations (from 50 pM to 50 nM) was incubated with folded 10 nM THRaptA and 15 nM THRaptB in HEPES buffer for 90 min prior to measurements. The thrombin/aptamer incubations were then added into the glass electrochemical cell. Before conducting voltammetric measurements, the sensor surface was allowed to react with analytes for 90 min. Selectivity tests with other proteins (IgE, insulin, or BSA), were made under the same conditions.

Figure 3A:
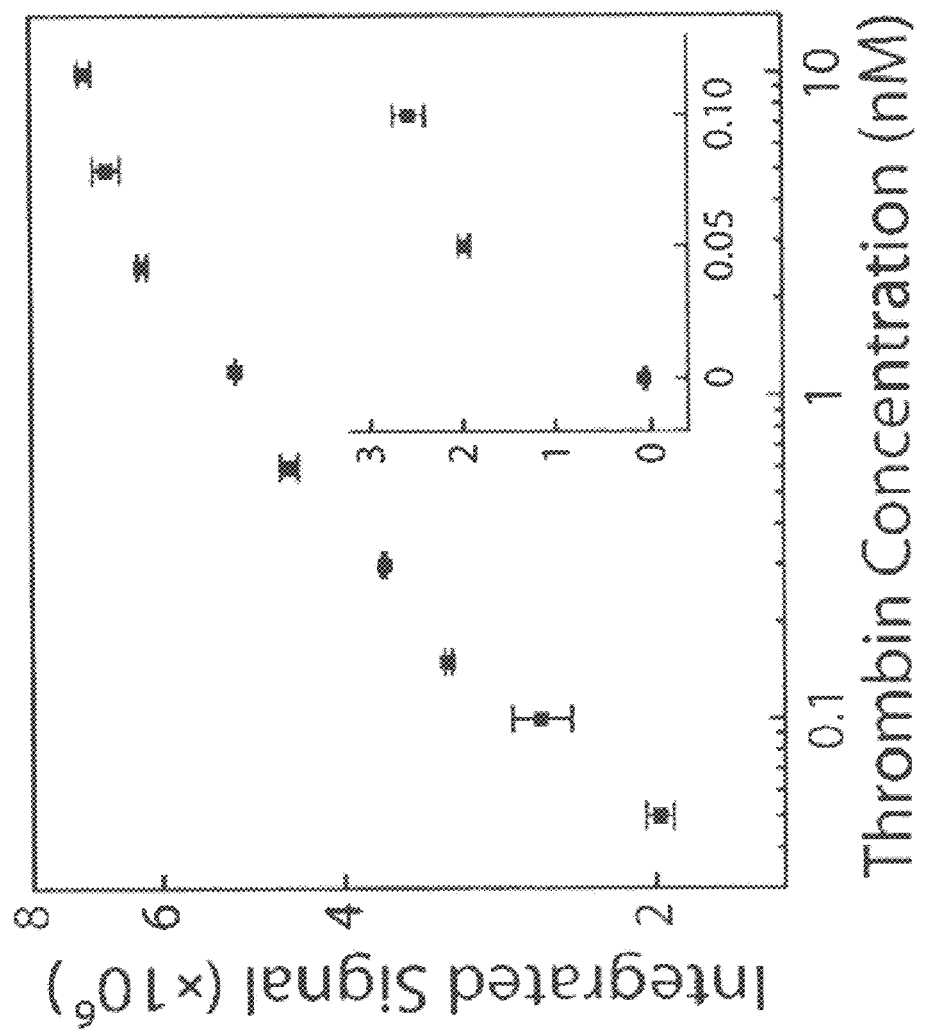
Figure 3C:
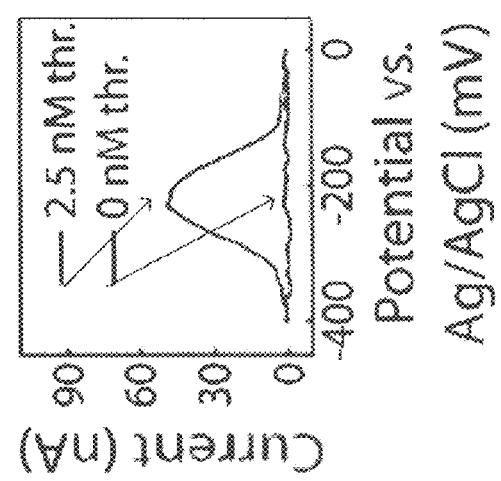

A schematic of aptamer-based ECPA is shown in FIG. 3B. Two thrombin aptamers (THRaptA, THRaptB) that bind thrombin at different sites were applied as affinity probes, and competitor C9 was used to minimize background. Using conditions optimized by the model system, background levels were measured in the absence of target protein (human thrombin). Similar to the model system, background remained at baseline current for up to 90 min, after which an increasing peak current at −210 mV was detected, indicating that MB-DNA was beginning to displace the competitors. This 90-min detection window was actually wider than the 40-min window observed in the model system. This difference is attributed to the decreased diffusion coefficient of the MB-DNA (40-bases; ~70 μm$^2$ s$^{-1}$) when hybridized with THRaptB (120-bases; ~30 μm$^2$ s$^{-1}$), which would slow the kinetics of the competitor displacement process by ~2.3-fold in comparison to the model system. This estimation agrees very well with the 2.25-fold increase in time required for background formation. FIG. 3C shows the background with no thrombin (lower trace) and a typical MB oxidation peak appearing at −210 mV (upper trace) in the presence of 2.5 nM thrombin after the 90 min incubation. As expected, the saturated peak current at 10 nM thrombin (52 nA) was of lower magnitude than the model system (81 nA), which had assumed probes with infinite affinity. This aptamer-based ECPA system was calibrated versus thrombin concentration (FIG. 3A), with sensor responses recorded in triplicate as integrated MB peak areas from −330 mV to −100 mV. ECPA was capable of detecting thrombin levels as low as 50 pM using a direct electrochemical readout, with a dynamic range up to 10 nM at these probe concentrations.

Figure 3D:
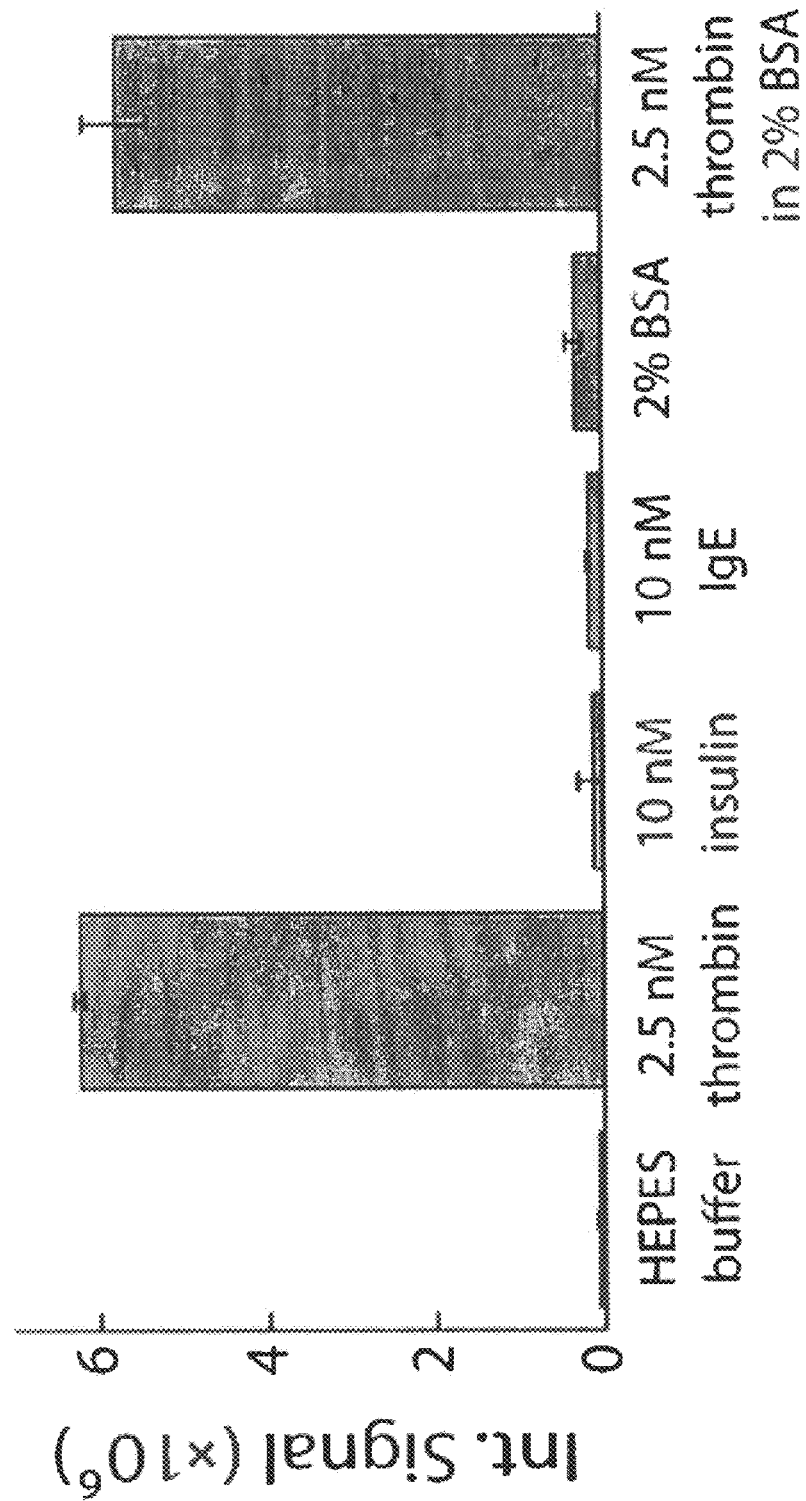

To demonstrate specificity, the aptamer-based ECPA was challenged with nonspecific proteins including human IgE, insulin, and BSA. FIG. 3D shows that essentially no response was observed in the presence of 10 nM insulin or IgE; even with 4-fold lower thrombin (2.5 nM), the signal was ~40-fold larger than that of IgE or insulin. In addition, baseline current was observed in the presence of 2% BSA, while the signal from 2.5 nM thrombin was recovered by 93% in 2% BSA. This result indicates application of ECPA to biological samples and point-of-care settings.

Example 3

To greatly improve the flexibility of ECPA, the system is proven functional with antibody-oligonucleotide conjugates as probes; the insulin detection limit is surprisingly low for a direct readout technique at about 128 fM with a dynamic range of over four orders of magnitude in concentration, again with high assay selectivity. ECPA thus allows separation-free, highly sensitive, and highly selective protein detection with a direct electrochemical readout. This method is extremely flexible, capable of detecting a wide variety of protein targets, and is amenable to point-of-care protein measurement, since any target with two aptamers, antibodies, or molecular recognition elements could be assayed via direct electrochemical readout.

For the antibody-based ECPA system, the sensor was equilibrated in 500 μl HEPES/NaClO$_4$ buffer with 300 nM C9 for 6 h. Prior to measurements, HEPES/NaClO$_4$ buffer was supplemented with 0.5% BSA (w/v) (to minimize antibody adsorption), 10 nM Ab1, 10 nM Ab2, 10 nM MB (for background measurements), and various concentrations of insulin (from 128 fM to 2 nM). Before conducting voltammetric measurements, the sensor surface was allowed to react with analytes for 40 min. Selectivity tests were performed in the same manner by substituting 2 nM C-peptide or insulin-like growth factor 1 (IGF-1) for insulin.

The flexibility of the aforementioned aptamer-based approach is somewhat limited because of the requirement of two aptamers for the target protein, since aptamer pairs exist only for a few select proteins. The use of antibody-oligonucleotide conjugates as probes can overcome this challenge. With the success of sandwich immunoassays, there exists a large, commercially available library of antibody pairs against many proteins. As proof of concept that ECPA can be applied to a wide variety of protein targets, the present disclosure shows that insulin can be directly detected using two antibody-oligonucleotide conjugates as ECPA probes.

Figure 4B:
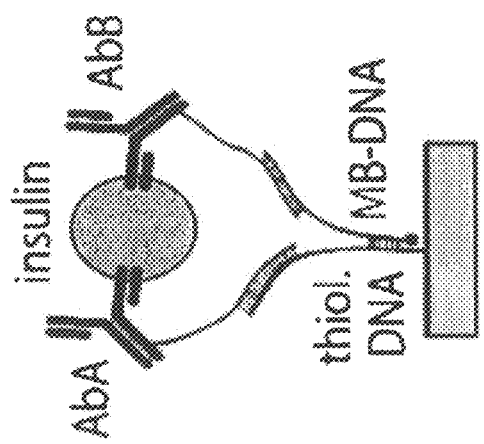
Figure 4C:
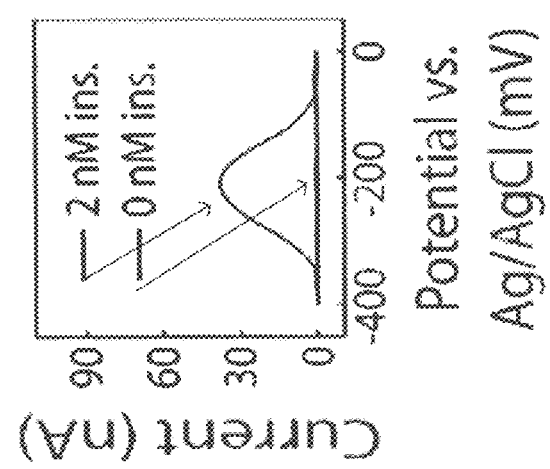
Figure 4D:
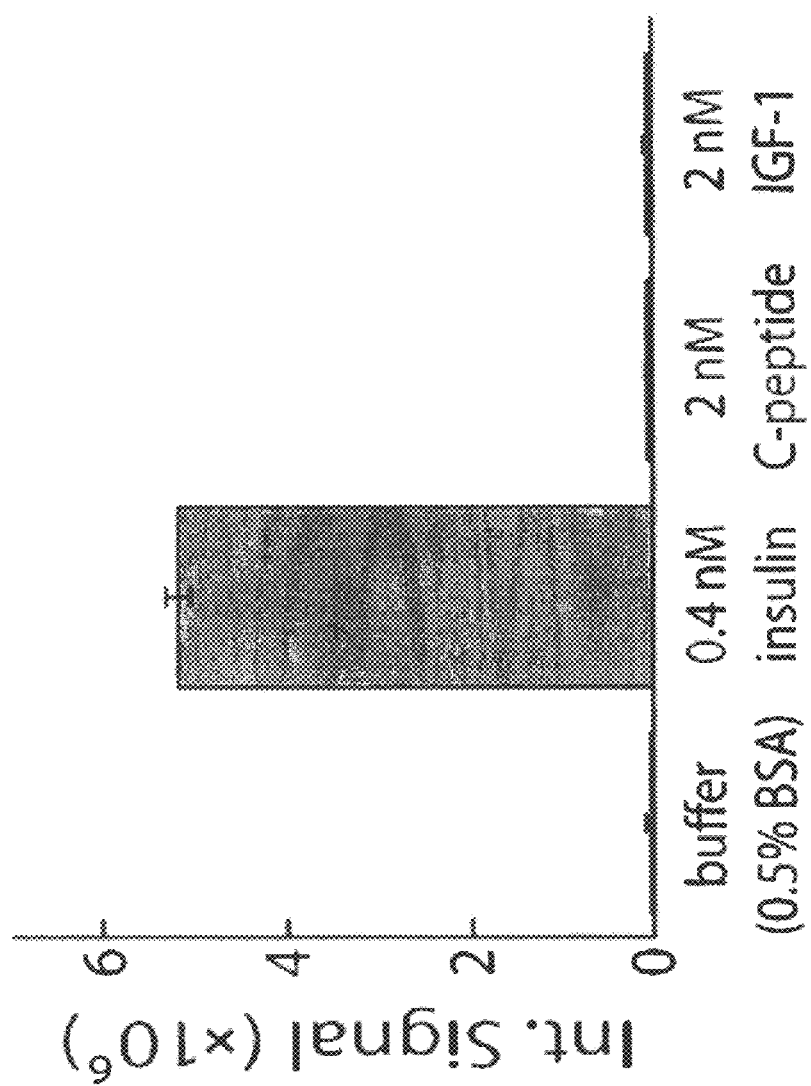

A schematic of antibody-based ECPA is shown in FIG. 4B. With this new assay format, a different set of conditions were determined as optimal, including the addition of 0.5% BSA to reduce nonspecific antibody adsorption and a C9 concentration of 300 nM. Using 10 nM of each antibody-oligo and 10 nM MB-DNA, the assay showed a 40-min detection window before competitor began to be displaced by MB-DNA. Since the antibody-oligo conjugates will significantly alter the diffusion rates of most components, it was not expected the kinetics of signal and background formation to follow trends observed in the model system or aptamer-based ECPA; nonetheless, the detection time window was similar to the other systems. FIG. 4C shows the background with no insulin (lower trace) and a typical MB oxidation peak appearing at −210 mV (upper trace) in the presence of 2 nM insulin after 40 min. This antibody-based ECPA system was then calibrated versus insulin concentration (FIG. 4A), with sensor response recorded in duplicate as integrated MB peak areas from −330 mV to −100 mV. Remarkably, using a direct electrochemical readout, ECPA was capable of detecting insulin levels as low as 128 fM (7.43×10$^{-4}$ ng mL$^{-1}$) with a dynamic range extending to 2 nM (11.6 ng mL$^{-1}$). The selectivity of antibody-based ECPA was tested against insulin-like growth factor 1 (IGF-1), which has similar structure to insulin, and against C-peptide, which is co-secreted with insulin into the bloodstream. As expected, the sensor did not respond to higher concentrations of either IGF-1 or C-peptide (FIG. 4D). Although the overall detection limit in the fM range was surprising for a direct-readout technique, the drastically improved performance of the antibody-based ECPA compared to the thrombin aptamer ECPA was expected, since the aptamer K$_d$ values are several orders of magnitude higher than the typical antibody K$_d$.

Finally, a comparison is provided between antibody-based ECPA and commercially available sandwich ELISAs for insulin detection. In order to facilitate equal comparison of the direct-readout ECPA with various heterogeneous ELISAs, the concentrations of insulin in the incubation solution of each ELISA is reported. ECPA outperforms all included kits in terms of assay dynamic range (from 43- to 312-fold wider range). The impressive ECPA dynamic range of 15 600 (from 128 fM to 2 nM) should provide enhanced flexibility in sample preparation. Only one of the "ultrasensitive" versions of ELISA (25 µL sample volume) has an essentially equal detection limit (1.1-fold higher) compared to ECPA. Compared to "standard" ELISA kits, ECPA shows between 15.6- and 60.9-fold lower limit of detection for insulin. In fact, using the noise level of the blank, the linearly extrapolated LOD for insulin using ECPA was calculated to be 20 fM, lower than all ELISAs. These performance improvements come with the additional benefit of a direct-readout format, making ECPA amenable to point-of-care analysis. Embodiments of ECPA of the present disclosure represent the highest performing direct-readout insulin assay reported to date, even without employing molecular amplification techniques.

Example 4

One property of tightly binding molecular recognition elements such as antibodies or aptamers is that binding can be nearly irreversible. With single-use sensors such as readouts at the point-of-care or in medical clinics, this is not typically a problem. On the other hand, in cases where continuous detection or reusable electrodes are needed, this property can be undesirable.

Another useful example of ECPA is the development of a reusable, or washable ECPA. In one embodiment, ECPA probes can be used for measurement then simply washed from the surface using deionized water, the appropriate aqueous buffer solution, or a solvent of choice. In another embodiment, probes can be washed with an additional DNA competitor strand that displaces the previously immobilized probe-DNA conjugates. In yet another embodiment, an enzyme can be used to digest, unwind, or remove the surface hybridized DNA, thereby resetting the sensor for loading of new probes. The frequency of reusable measurements will be dependent upon the washing or probe resetting methodology. The present disclosure includes a system for ECPA measurements as quickly as every few seconds with the appropriate washing and surface regenerating fluidic system, such as a microfluidic system.

A specific example of reusable ECPA is the use of uracil-containing DNA strands to immobilize the proximity probes. The segments of DNA that are complementary to the surface-immobilized DNA strand are made to incorporate uracil (U) instead of thymine (T). The U-containing sections of DNA retain base-pairing complementarity with adenines (A) on the immobilized DNA, but they are susceptible to degradation with enzymes or enzyme mixtures. One example of an enzyme mixture is the commercially available Uracil-DNA Excision Mix (Epicentre), which includes uracil-DNA glycosylase to remove U bases and endonuclease IV to cleave DNA at this abasic site. Thus, strands where U is present in place of T will be cleaved at that substitution. To accomplish reusable ECPA, U-containing probes can be enzymatically removed with these types of enzyme mixtures, probes can be reloaded, and measurements can be quickly repeated. This strategy has allowed ECPA measurements to be accomplished in continuous 3 minute increments, and optimization is likely to allow sub-minute reusable ECPA. Another advantage of this approach is that the originally surface immobilized DNA can be left unharmed, thus minimizing effects of repeated surface preparation.

Example 5

ECPA as described herein incorporates electrochemical readout. However, the present disclosure includes other forms of detection. In one embodiment, similar surface-based proximity assays could be developed for readout by surface plasmon resonance (SPR), particularly since the example using gold electrodes is directly amenable to SPR. This would allow more rapid interrogation of the system and/or characterization of the dynamics of surface binding and hybridization. In another embodiment, Raman spectroscopy could be employed for detection of proximity binding of target proteins or peptides. This would provide the possibility for higher order multiplexing of the assay using only one probe. It is feasible that various other surface-based measurement techniques could be substituted for electrochemical measurements using a probe assembly similar to that shown in FIG. 1A, 3B, or 4B, as would be understood by one skilled in the art.

Yet another embodiment of ECPA or similar surface-based readouts would be a densely arrayed format that could allow quantitative imaging of protein levels with high spatial resolution.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In an embodiment, the term "about" can include traditional rounding according to the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of the disclosure. Many variations and modifications may be made to the above-described embodiments. All such modifications and variations are intended to be included herein within the scope of this disclosure and protected by the following claims.

Therefore, at least the following is claimed:

1. An electrochemical proximity assay (ECPA) comprising:
   forming a nucleic acid layer, wherein the nucleic acid layer comprises at least one short single stranded nucleic acid competitor, on an electrically conductive base;
   generating an electrical signal by immersing the electrically conductive base comprising the nucleic acid layer into a solution comprising at least one ECPA probe and at least one target, wherein the nucleic acid layer, at least one ECPA probe, and at least one target form a complex; and
   quantifying an amount of the target by analyzing the electrical signal, wherein the electrical signal changes in proportion to changes in the concentration of the target.

2. The ECPA of claim 1, wherein the nucleic acid layer comprises at least one surface immobilized nucleic acid strand.

3. The ECPA of claim 2, wherein the surface immobilized nucleic acid strand is selected from the group consisting of: thiolated DNA, amine labeled DNA, RNA, modified RNA, and a combination thereof.

4. The ECPA of claim 1, wherein the nucleic acid layer is formed by covalent attachment of the nucleic acid to the electrically conductive base.

5. The ECPA of claim 1, wherein the electrically conductive base is selected from the group consisting of: a metal electrode, an activated carbon electrode, a conductive ceramic, a conductive glass, and a combination thereof.

6. The ECPA of claim 1, wherein the ECPA probe comprises at least one molecular recognition element specific to the target and at least one nucleic acid/electron transfer conjugate.

7. The ECPA of claim 1, wherein the nucleic acid competitor has complementary bases with at least one nucleic acid strand in the nucleic acid layer.

8. The ECPA of claim 7, wherein the nucleic acid competitor has 5 to 50 complementary bases with at least one nucleic acid strand in the nucleic acid layer.

9. The ECPA of claim 1, wherein the competitor nucleic acid impedes the hybridization of at least one nucleic acid/electron transfer conjugate.

10. The ECPA of claim 9, wherein the target causes the nucleic acid/electron transfer conjugate to move closer to a surface of the electrically conductive base, replacing the competitor nucleic acid, and allowing an electron transfer process.

11. The ECPA of claim 1, wherein the target is selected from the group consisting of: a protein, a small molecule, a multi-protein complex, a nucleic acid, a polymer, a whole cell, a virus, a biological polymer, and a combination thereof.

12. The ECPA of claim 1, wherein quantification of the target is used in the treatment of health related issues selected from the group consisting of: heart attack, stroke, rhabdomylosis, fertility, diabetes, obesity, metabolic syndrome, sepsis, inflammatory response, food safety, tuberculosis, and a combination thereof.

13. The ECPA of claim 1, wherein multiple targets are quantified simultaneously.

14. The ECPA of claim 1, wherein the complex is re-usable.

15. The ECPA of claim 14, wherein the complex is used for measurement, then washed with a solvent so that the complex is re-useable.

16. The ECPA of claim 14, wherein the complex is washed with a DNA competitor strand, wherein the DNA competitor strand displaces the previously immobilized ECPA probe.

17. The ECPA of claim 6, wherein the at least one molecular recognition element is selected from the group consisting of: an aptamer, an antibody, an antibody/DNA conjugate, and a combination thereof.

18. A method for quantifying a target in a sample comprising:
mixing a nucleic acid with a competitor DNA;
immobilizing the nucleic acid/competitor DNA on an electrically conductive base to form a nucleic acid/competitor DNA layer;
mixing the target with at least one molecular recognition element and at least one nucleic acid/electron transfer conjugate to form a probe/target solution;
immersing the electrically conductive base comprising the nucleic acid/competitor DNA layer into the probe/target solution to generate an electrical signal; and
quantifying the target by analyzing the electrical signal, wherein the electrical signal increases in proportion to the concentration of the target.

19. The method of claim 18, wherein the target is identified by analyzing the electrical signal.

20. The method of claim 18, wherein the at least one molecular recognition element is selected from the group consisting of: an aptamer, an antibody, an antibody/DNA conjugate, and a combination thereof.

21. The method of claim 18, wherein the competitor DNA comprises complementary bases with the nucleic acid.

22. The method of claim 18, wherein the sample comprises a biological sample selected from the group consisting of: blood serum, whole blood, nasal aspirates, saliva, urine, feces, cell lysate, dialysis sampling, tissue biopsy, cell media, and a combination thereof.

23. The method of claim 22, wherein the biological sample is unprocessed.

24. The method of claim 18, wherein the target is selected from the group consisting of: a peptide, a protein, a small molecule, a whole cell, a multi-protein complex, a nucleic acid, a virus, and a combination thereof.

25. The method of claim 18, wherein the method is used at the point-of-care (POC) to detect biomarkers of disease.

26. The method of claim 18, wherein a concentration of target in the sample as low as about 1 attomolar ($10^{-18}$ mol/dm$^3$) is detected.

27. A complex comprising:
a surface immobilized nucleic acid layer, wherein the nucleic acid layer comprises at least one short single stranded nucleic acid competitor in the surface immobilized nucleic acid layer, wherein the nucleic acid competitor has complementary bases with the surface immobilized nucleic acid;
a first molecular recognition element;
a target;
a second molecular recognition element; and
a nucleic acid/electron transfer conjugate.

28. The complex of claim 27, wherein the surface immobilized nucleic acid layer is covalently attached to an electrically conductive base, the first and second molecular recognition elements are specific to and bound to the target, and the complex comprises a circular structure on the electrically conductive base through proximity dependent hybridization of the surface immobilized nucleic acid and the nucleic acid/electron transfer conjugate.

29. The complex of claim 27, wherein the nucleic acid layer comprises at least one surface immobilized nucleic acid strand, and wherein the surface immobilized nucleic acid strand is selected from the group consisting of: a thiolated DNA, an amine labeled DNA, an RNA, a modified RNA, and a combination thereof.

30. The complex of claim 27, wherein the nucleic acid/electron transfer conjugate comprises a methylene blue conjugated DNA (MB-DNA).

31. The complex of claim 27, wherein the first and second molecular recognition elements are each independently selected from the group consisting of: an aptamer, an antibody, an antibody/DNA conjugate, and a combination thereof.

32. The complex of claim 27, wherein the target is selected from the group consisting of: a peptide, a protein, a small molecule, a whole cell, a multi-protein complex, a nucleic acid, a virus, and a combination thereof.

* * * * *

SEQUENCE LISTING

```
<160> NUMBER OF SEQ ID NOS: 4

<210> SEQ ID NO 1
<211> LENGTH: 80
<212> TYPE: DNA
<213> ORGANISM: ARTIFICIAL SEQUENCE
```

```
<220> FEATURE:
<223> OTHER INFORMATION: Chemically synthesized Thrombin aptamer

<400> SEQUENCE: 1
agtccgtggt agggcaggtt ggggtgactt tttttttttt tttttatatt ttttttttct    60
cgcggatttg aaccctaacg                                                80

<210> SEQ ID NO 2
<211> LENGTH: 80
<212> TYPE: DNA
<213> ORGANISM: ARTIFICIAL SEQUENCE
<220> FEATURE:
<223> OTHER INFORMATION: Chemically synthesized thrombin aptamer

<400> SEQUENCE: 2
taggaaaagg aggagggtgg gattggtgtg tgtttttttt tttttttttt tttttttttt    60
tttttggttg gtgtggttgg                                                80

<210> SEQ ID NO 3
<211> LENGTH: 40
<212> TYPE: DNA
<213> ORGANISM: ARTIFICIAL SEQUENCE
<220> FEATURE:
<223> OTHER INFORMATION: Chemically synthesized thrombin aptamer

<400> SEQUENCE: 3
cccacttaaa cctcaatcca cgcggatttg aaccctaacg                          40

<210> SEQ ID NO 4
<211> LENGTH: 40
<212> TYPE: DNA
<213> ORGANISM: ARTIFICIAL SEQUENCE
<220> FEATURE:
<223> OTHER INFORMATION: Chemically synthesized thrombin aptamer

<400> SEQUENCE: 4
taggaaaagg aggagggtgg cccacttaaa cctcaatcca                          40
```